(12) United States Patent
Felix et al.

(10) Patent No.: US 12,171,562 B1
(45) Date of Patent: *Dec. 24, 2024

(54) ELECTROCARDIOGRAMY PATCH

(71) Applicant: Bardy Diagnostics, Inc., Bellevue, WA (US)

(72) Inventors: Jason Felix, Vashon Island, WA (US); Jon Mikalson Bishay, Seattle, WA (US); Gust H. Bardy, Carnation, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/821,409

(22) Filed: Aug. 30, 2024

Related U.S. Application Data

(63) Continuation of application No. 18/647,762, filed on Apr. 26, 2024, now Pat. No. 12,089,943, which is a
(Continued)

(51) Int. Cl.
*A61B 5/335* (2021.01)
*A61B 5/00* (2006.01)
(Continued)

(52) U.S. Cl.
CPC ............ *A61B 5/335* (2021.01); *A61B 5/0006* (2013.01); *A61B 5/0022* (2013.01);
(Continued)

(58) Field of Classification Search
CPC .... A61B 2560/0214; A61B 2560/0443; A61B 5/0006; A61B 5/0022; A61B 5/02055;
(Continued)

(56) References Cited

U.S. PATENT DOCUMENTS

| 5,862,803 A | 1/1999 | Besson et al. |
|---|---|---|
| 7,197,357 B2 | 3/2007 | Istvan et al. |

(Continued)

FOREIGN PATENT DOCUMENTS

| WO | 2003065926 A2 | 8/2003 |
|---|---|---|
| WO | 2008005015 A1 | 1/2008 |

(Continued)

OTHER PUBLICATIONS

Anand et al., "Design of the Multi-Sensor Monitoring in Congestive Heart Failure (Music) Study: Prospective Trial to Assess the Utility of Continuous Wireless Physiologic Monitoring in Heart Failure", Journal of Cardiac Failure, vol. 17, No. 1, Jan. 1, 2011, pp. 11-16 (6 pages).

(Continued)

*Primary Examiner* — George Manuel
(74) *Attorney, Agent, or Firm* — K&L Gates LLP

(57) ABSTRACT

An apparatus is provided. A strip has first and second end sections, and a first face and second face. Two electrocardiographic electrodes are provided on the strip with one of the electrocardiographic electrodes provided on the first face of the first end section of the strip and another of the electrocardiographic electrodes positioned on the first face on the second end section of the strip. A flexible circuit is mounted to the second face of the strip and includes a circuit trace electrically coupled to each of the electrocardiographic electrodes. The apparatus includes a wireless transceiver and a battery.

30 Claims, 8 Drawing Sheets

Related U.S. Application Data continuation of application No. 18/353,398, filed on Jul. 17, 2023, which is a continuation of application No. 17/946,933, filed on Sep. 16, 2022, now Pat. No. 11,723,575, which is a continuation of application No. 17/367,476, filed on Jul. 5, 2021, now Pat. No. 11,445,967, which is a continuation of application No. 17/119,945, filed on Dec. 11, 2020, now Pat. No. 11,051,743, which is a continuation of application No. 16/241,929, filed on Jan. 7, 2019, now Pat. No. 10,888,239, which is a continuation of application No. 15/818,437, filed on Nov. 20, 2017, now Pat. No. 10,172,534, which is a continuation of application No. 15/256,266, filed on Sep. 2, 2016, now Pat. No. 9,820,665, which is a continuation of application No. 14/082,071, filed on Nov. 15, 2013, now Pat. No. 9,433,367, which is a continuation-in-part of application No. 14/080,717, filed on Nov. 14, 2013, now Pat. No. 9,545,204, and a continuation-in-part of application No. 14/080,725, filed on Nov. 14, 2013, now Pat. No. 9,730,593.

(60) Provisional application No. 61/882,403, filed on Sep. 25, 2013.

(51) Int. Cl.
| | | |
|---|---|---|
| *A61B 5/0205* | (2006.01) | |
| *A61B 5/145* | (2006.01) | |
| *A61B 5/259* | (2021.01) | |
| *A61B 5/282* | (2021.01) | |
| *G16H 40/67* | (2018.01) | |
| *A61B 5/021* | (2006.01) | |
| *A61B 5/03* | (2006.01) | |
| *A61B 5/08* | (2006.01) | |
| *A61B 5/087* | (2006.01) | |
| *A61B 5/11* | (2006.01) | |
| *A61B 5/1455* | (2006.01) | |
| *A61B 5/349* | (2021.01) | |

(52) U.S. Cl.
CPC ...... *A61B 5/02055* (2013.01); *A61B 5/14532* (2013.01); *A61B 5/14542* (2013.01); *A61B 5/259* (2021.01); *A61B 5/282* (2021.01); *A61B 5/6823* (2013.01); *A61B 5/6833* (2013.01); *A61B 5/7405* (2013.01); *A61B 5/7455* (2013.01); *A61B 5/7475* (2013.01); *G16H 40/67* (2018.01); *A61B 5/021* (2013.01); *A61B 5/03* (2013.01); *A61B 5/0816* (2013.01); *A61B 5/087* (2013.01); *A61B 5/1118* (2013.01); *A61B 5/14551* (2013.01); *A61B 5/349* (2021.01); *A61B 2560/0214* (2013.01); *A61B 2560/0443* (2013.01)

(58) Field of Classification Search
CPC ......... A61B 5/021; A61B 5/03; A61B 5/0816; A61B 5/087; A61B 5/1118; A61B 5/14532; A61B 5/14542; A61B 5/14551; A61B 5/259; A61B 5/282; A61B 5/335; A61B 5/349; A61B 5/6823; A61B 5/6833; A61B 5/7405; A61B 5/7455; A61B 5/7475; G16H 40/63; G16H 40/67
See application file for complete search history.

(56) References Cited

U.S. PATENT DOCUMENTS

| | | |
|---|---|---|
| 7,206,630 B1 | 4/2007 | Tarler |
| 7,212,849 B2 | 5/2007 | Zhang et al. |
| 7,395,106 B2 | 7/2008 | Ryu et al. |
| 7,468,032 B2 | 12/2008 | Stahmann et al. |
| 8,150,502 B2 | 4/2012 | Kumar et al. |
| 8,214,007 B2 | 7/2012 | Baker et al. |
| 8,315,695 B2 | 11/2012 | Sebelius et al. |
| 8,483,809 B2 | 7/2013 | Kim et al. |
| 8,538,503 B2 | 9/2013 | Kumar et al. |
| 8,560,046 B2 | 10/2013 | Kumar et al. |
| 8,611,980 B2 | 12/2013 | Choe et al. |
| 8,630,699 B2 | 1/2014 | Baker et al. |
| 8,647,268 B2 | 2/2014 | Tran |
| 8,718,742 B2 | 5/2014 | Beck et al. |
| 8,750,974 B2 | 6/2014 | Baker et al. |
| 8,926,509 B2 | 1/2015 | Magar et al. |
| 8,965,492 B2 | 2/2015 | Baker et al. |
| 9,149,229 B1 | 10/2015 | Tarler |
| 9,155,484 B2 | 10/2015 | Baker et al. |
| 9,211,073 B2 | 12/2015 | Banet et al. |
| 9,241,649 B2 | 1/2016 | Kumar et al. |
| 9,277,864 B2 | 3/2016 | Yang et al. |
| 9,433,366 B2 | 9/2016 | Baker et al. |
| 9,510,755 B2 | 12/2016 | Fong et al. |
| 9,669,212 B2 | 6/2017 | Mueller et al. |
| 9,693,732 B1 | 7/2017 | Tarler |
| 9,877,663 B2 | 1/2018 | Baker et al. |
| 10,159,422 B2 | 12/2018 | Baker et al. |
| 10,327,660 B2 | 6/2019 | Gallego et al. |
| 10,405,799 B2 | 9/2019 | Kumar et al. |
| 10,413,251 B2 | 9/2019 | Golda et al. |
| 10,441,185 B2 | 10/2019 | Rogers et al. |
| 10,517,500 B2 | 12/2019 | Kumar et al. |
| 10,939,839 B2 | 3/2021 | Baker et al. |
| 11,051,743 B2 | 7/2021 | Felix et al. |
| 11,116,447 B2 | 9/2021 | Yang et al. |
| 11,141,091 B2 | 10/2021 | Kumar et al. |
| 11,445,967 B2 | 9/2022 | Felix et al. |
| 2002/0072682 A1* | 6/2002 | Hopman .......... A61B 5/25 600/509 |
| 2008/0091089 A1 | 4/2008 | Guillory et al. |
| 2009/0062670 A1 | 3/2009 | Sterling et al. |
| 2009/0099469 A1 | 4/2009 | Flores |
| 2009/0177073 A1 | 7/2009 | Sonnenborg |
| 2009/0182204 A1 | 7/2009 | Semler et al. |
| 2011/0009729 A1 | 1/2011 | Shin et al. |
| 2011/0054285 A1 | 3/2011 | Searle et al. |
| 2011/0077497 A1 | 3/2011 | Oster et al. |
| 2011/0125040 A1 | 5/2011 | Crawford et al. |
| 2012/0215123 A1 | 8/2012 | Kumar et al. |
| 2012/0323098 A1 | 12/2012 | Moein et al. |
| 2013/0225967 A1 | 8/2013 | Esposito |
| 2013/0226018 A1 | 8/2013 | Kumar et al. |
| 2015/0022372 A1 | 1/2015 | Vosch |
| 2015/0087950 A1 | 3/2015 | Felix et al. |
| 2016/0029917 A1 | 2/2016 | Baker et al. |
| 2019/0223806 A1 | 7/2019 | Bennet et al. |
| 2021/0315504 A1 | 10/2021 | Kumar et al. |

FOREIGN PATENT DOCUMENTS

| | | |
|---|---|---|
| WO | 2008057884 A2 | 5/2008 |
| WO | 2010104952 A2 | 9/2010 |

OTHER PUBLICATIONS

Cesario et al., "Arrhythmia Detection with a Low-Profile Wireless Adherent Cardiac Monitor: Results from the Adam and Eve Studies", The Journal of Innovations in Cardiac Rhythm Management, 2 (2011) Sep. 2011, pp. 476-482, (7 pages).

Corventis Nuvant, "Nuvant Mobile Cardiac Telementry (MTC) System", Corventis, 2009, last printed Jul. 18, 2024, https://web.archive.org/web/20100127193736/http://corventis.com/AP/nuvant.asp.

Corventis Avivo, "Avivo Mobile Patient Management System", Corventis, 2008, lasted printed Jul. 18, 2024, https://web.archive.org/web/20100118155329/http://www.corventis.com/AP/avivo.asp.

(56) References Cited

OTHER PUBLICATIONS

IRhythm Zio XT Patch/Event Card, "Zio Patch", iRhythm, 2011, last printed Jul. 18, 2024, https://web.archive.org/web/20111017074139/http://irhythmtech.com/media/files/Z100A4020.04%20-%20ZIO%20PATCH%20DATA%20SHEET.pdf.
*Bardy Diagnostics, Inc.* v. *Vital Connect, Inc.*, Defendant's Identification of Supplemental Prior Art References, C.A. No. 22-351 (CJV), May 22, 2024.
International Preliminary Report on Patentability and Written Opinion, PCT/US2019/064331, Jun. 8, 2021.
First Examination Report, Communication pursuant to Article 94(3) EPC, 19 828 053.9-1113, dated Apr. 15, 2024.
"23 Personal Tools to Learn More About Yourself," Flowingdata.com, Sep. 18, 2008, 18 pages.
Adams et al., U.S. Appl. No. 61/755,623, filed Jan. 23, 2013, 48 pages.
Alzaidi et al., "Smart Textiles Based Wireless ECG System," May 2012; 5 pages.
Au-Yeung et al., U.S. Appl. No. 60/765,467, filed Feb. 6, 2006, 25 pages.
Aventyn, Inc., "Vital Connect, Aventyn Launch Wearable Biosensor Platform for Mobile Patient Monitoring", Dec. 12, 2013, 5 pages.
*Bardy Diagnostics, Inc.*, Plaintiff v. *Vital Connect, Inc.*; The United States District Court for the District of Delaware; C.A. No. 22-351 (CJB); Vitalconnect's Preliminary Invalidity Contentions; filed Oct. 25, 2023.
Chaimanonart et al., "A Wireless Batteryless in vivo EKG and Body Temperature Sensing Microsystem with Adaptive RF Powering for Genetically Engineered Mice Monitoring," Jul. 2009; 4 pages.
Chart A-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar"); Oct. 25, 2023; 19 pages.
Chart A-2 Invalidity Contentions: U.S. Pat. No. 11,051,743; Case No. 22-351-CJB (Delaware); Invalidity of U.S. Pat. No. 11,051,743 by U.S. Pat. No. 11,116,447 ("Yang"); Oct. 25, 2023; 19 pages.
Chart A-3 Invalidity Contentions: U.S. Pat. No. 11,051,743; Case No. 22-351-CJB (Delaware); Invalidity of U.S. Pat. No. 11,051,743 by U.S. Pat. No. 10,327,660 ("Gallego"); Oct. 25, 2023; 12 pages.
Chart A-3 Invalidity Contentions: U.S. Pat. No. 11,445,967; Case No. 22-351-CJB (Delaware); Invalidity of U.S. Pat. No. 11,445,967 by U.S. Pat. No. 10,327,660 ("Gallego"); Oct. 25, 2023; 7 pages.
Chart A-4 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster"); Oct. 25, 2023; 11 pages.
Chart A-4 Invalidity Contentions: U.S. Pat. No. 11,445,967; Case No. 22-351-CJB (Delaware); Invalidity of U.S. Pat. No. 11,445,967 by U.S. Pat. Pub. No. 2011/0077497 ("Oster"); Oct. 25, 2023; 6 pages.
Chart A-5 Invalidity Contentions: U.S. Pat. No. 11,051,743; Case No. 22-351-CJB (Delaware); Invalidity of U.S. Pat. No. 11,051,743 by U.S. Pat. No. 10,413,251 ("Golda"); Oct. 25, 2023; 11 pages.
Chart A-6 Invalidity Contentions: U.S. Pat. No. 11,051,743; Case No. 22-351-CJB (Delaware); Invalidity of U.S. Pat. No. 11,051,743 by U.S. Pat. No. 9,669,212 ("Mueller"); Oct. 25, 2023; 11 pages.
Chart A-7 Invalidity Contentions: U.S. Pat. No. 11,051,743; Case No. 22-351-CJB (Delaware); Invalidity of U.S. Pat. No. 11,051,743 by U.S. Pat. No. 7,206,630 ("Tarler"); Oct. 25, 2023; 12 pages.
Chart A-8 Invalidity Contentions: U.S. Pat. No. 11,051,743; Case No. 22-351-CJB (Delaware); Invalidity of U.S. Pat. No. 11,051,743 by WO 2008/005015 ("Shennib"); Oct. 25, 2023; 12 pages.
Chart A-9 Invalidity Contentions: U.S. Pat. No. 11,051,743; Case No. 22-351-CJB (Delaware); Invalidity of U.S. Pat. No. 11,051,743 by U.S. Pat. Pub. No. 2011/0009729 ("Shin"); Oct. 25, 2023; 12 pages.
Chart A-10 Invalidity Contentions: U.S. Pat. No. 11,051,743; Case No. 22-351-CJB (Delaware); Invalidity of U.S. Pat. No. 11,051,743 by WO 2003/065926 ("Ozguz"); Oct. 25, 2023; 12 pages.
Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar"); Oct. 25, 2023; 13 pages.
Chart AA-2 Invalidity Contentions: U.S. Pat. No. 11,445,967; Case No. 22-351-CJB (Delaware); Invalidity of U.S. Pat. No. 11,445,967 by U.S. Patent No. 11, 116,447 ("Yang"); Oct. 25, 2023; 14 pages.
Chart AA-5 Invalidity Contentions: U.S. Pat. No. 11,445,967; Case No. 22-351-CJB (Delaware); Invalidity of U.S. Pat. No. 11,445,967 by U.S. Pat. No. 10,413,251 ("Golda"); Oct. 25, 2023; 6 pages.
Chart AA-6 Invalidity Contentions: U.S. Pat. No. 11,445,967; Case No. 22-351-CJB (Delaware); Invalidity of U.S. Pat. No. 11,445,967 by U.S. Pat. No. 9,669,212 ("Mueller"); Oct. 25, 2023; 6 pages.
Chart AA-7 Invalidity Contentions: U.S. Pat. No. 11,445,967; Case No. 22-351-CJB (Delaware); Invalidity of U.S. Pat. No. 11,445,967 by U.S. Pat. No. 7,206,630 ("Tarler"); Oct. 25, 2023; 7 pages.
Chart AA-8 Invalidity Contentions: U.S. Pat. No. 11,445,967; Case No. 22-351-CJB (Delaware); Invalidity of U.S. Pat. No. 11,445,967 by WO 2008/005015 ("Shennib"); Oct. 25, 2023; 6 pages.
Chart AA-9 Invalidity Contentions: U.S. Pat. No. 11,445,967; Case No. 22-351-CJB (Delaware); Invalidity of U.S. Pat. No. 11,445,967 by U.S. Pat. Pub. No. 2011/0009729 ("Shin"); Oct. 25, 2023; 6 pages.
Chart AA-10 Invalidity Contentions: U.S. Pat. No. 11,445,967; Case No. 22-351-CJB (Delaware); Invalidity of U.S. Pat. No. 11,445,967 by WO 2003/065926 ("Ozguz"); Oct. 25, 2023; 6 pages.
Chart B-1 Invalidity Contentions: U.S. Pat. No. 11,051,743 and U.S. Pat. No. 11,445,967; Case No. 22-351-CJB (Delaware); Elongated Strip With Narrowed Midsection; Oct. 25, 2023; 8 pages.
Chart B-2 Invalidity Contentions: U.S. Pat. No. 11,051,743 and U.S. Pat. No. 11,445,967; Case No. 22-351-CJB (Delaware); An Electrocardiogramactrode on Each End of The Backing; Oct. 25, 2023; 8 pages.
Chart B-3 Invalidity Contentions: U.S. Pat. No. 11,051,743 and U.S. Pat. No. 11,445,967; Case No. 22-351-CJB (Delaware); Flexible Circuit Comprising a Pair of Circuit Traces to Couple Electrodes; Oct. 25, 2023; 8 pages.
Chart B-4 Invalidity Contentions: U.S. Pat. No. 11,051,743 and U.S. Pat. No. 11,445,967; The Case No. 22-351-CJB (Delaware); Rounded Outer Edge of Backing Ends; Oct. 25, 2023; 5 pages.
Chart B-5 Invalidity Contentions: U.S. Pat. No. 11,051,743 and U.S. Pat. No. 11,445,967; Case No. 22-351-CJB (Delaware); Conversion of Electrocardiogramals From One Format to Another; Oct. 25, 2023; 6 pages.
Chart B-6 Invalidity Contentions: U.S. Pat. No. 11,051,743 and U.S. Pat. No. 11,445,967; Case No. 22-351-CJB (Delaware); Hydrocolloid Adhesives on a Portion of the Backing; Oct. 25, 2023; 5 pages.
Chart B-7 Invalidity Contentions: U.S. Pat. No. 11,051,743 and U.S. Pat. No. 11,445,967; Case No. 22-351-CJB (Delaware); A Patch Comprising Adhered Layers; Oct. 25, 2023; 16 pages.
Chart C-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar") and U.S. Pat. No. 11,116,447 ("Yang"); Oct. 25, 2023; 32 pages.
[Corrected] Chart C-2 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster") and U.S. Pat. No. 11,116,447 ("Yang"); Oct. 25, 2023; 22 pages.
[Corrected] Chart CC-2 Invalidity Contentions: U.S. Pat. No. 11,445,967; Case No. 22-351-CJB (Delaware); Invalidity of U.S. Patent No. by U.S. Pat. Pub. No. 2011/0077497 ("Oster") and U.S. Pat. No. 11,116,447 ("Yang"); Oct. 25, 2023; 16 pages.
Hill, "Adventures in Self-Surveillance: Fitbit, Tracking My Movement and Sleep," Forbes, Feb. 25, 2011, 11 pages.
Knight et al., U.S. Appl. No. 60/786,502, filed Mar. 29, 2006, 8 pages.
Mehen, "Open Health with the Quantified Self," Opensource.com, Aug. 25, 2011, 7 pages.
Mukala et al., "A Novel Zigbee-Based Low-Cost, Low-Power Wireless EKG System," IEEE, May 2010; 4 pages.
Pandian et al., "Wireless Sensor Network for Wearable Physiological Monitoring," Journal of Networks, vol. 3, No. 5, May 2008; 15 pages.

(56) References Cited

OTHER PUBLICATIONS

Puurtinen et al., "Estimation of ECG Signal of Closely Separated Bipolar Electrodes Using Thorax Models," Proceedings of the 26th Annual International Conference of the IEEE EMBS pp. 801-804, San Francisco, Calif., USA, Sep. 1-5, 2004, 4 pages.
Saeed et al., "A Scalable Wireless Body Area Sensor Network for Health-Care Monitoring," Jun. 2009, 4 pages.
Toth et al., U.S. Appl. No. 61/832,131, filed Jun. 6, 2013, 82 pages.
Trägårdh et al., How Many ECG Leads Do We Need?Cardiology Clinics. Aug. 2006; 24(3): 317-30, vii. doi: 10.1016/j.ccl.2006.04.005. PMID: 16939826; 14 pages.
Vishnubhotla, "Pre-Processing of ECG Signals for Ambulatory Use," Jan. 2009; 5 pages.
Wolf, "The Data-Driven Life," New York Times Magazine, Apr. 28, 2010, 13 pages.

\* cited by examiner

ELECTROCARDIOGRAMY PATCH

PRIORITY CLAIM AND CROSS-REFERENCE TO RELATED APPLICATIONS

This application is a continuation of U.S. patent application Ser. No. 18/647,762, filed Apr. 26, 2024, titled ELECTROCARDIOGRAPHY PATCH, which is a continuation of U.S. patent application Ser. No. 18/353,398, filed Jul. 17, 2023, titled ELECTROCARDIOGRAPHY PATCH, which is a continuation of U.S. patent application Ser. No. 17/946,933, filed Sep. 16, 2022, titled ELECTROCARDIOGRAPHY PATCH, which is a continuation of U.S. patent application Ser. No. 17/367,476, filed Jul. 5, 2021, titled ELECTROCARDIOGRAPHY PATCH, which is a continuation of U.S. patent application Ser. No. 17/119,945, filed Dec. 11, 2020, titled ELECTROCARDIOGRAPHY PATCH, which is a continuation of U.S. patent application Ser. No. 16/241,929, filed Jan. 7, 2019, titled REMOTE INTERFACING ELECTROCARDIOGRAPHY PATCH, which is a continuation of U.S. patent application Ser. No. 15/818,437, filed Nov. 20, 2017, titled REMOTE INTERFACING ELECTROCARDIOGRAPHY PATCH, which is a continuation of U.S. patent application Ser. No. 15/256,266, filed Sep. 2, 2016, titled REMOTE INTERFACING OF EXTENDED WEAR ELECTROCARDIOGRAPHY AND PHYSIOLOGICAL SENSOR MONITOR, which is a continuation of U.S. patent application Ser. No. 14/082,071, filed Nov. 15, 2013, titled REMOTE INTERFACING OF EXTENDED WEAR ELECTROCARDIOGRAPHY AND PHYSIOLOGICAL SENSOR MONITOR, which is a continuation-in-part of U.S. patent application Ser. No. 14/080,717, filed Nov. 14, 2013, titled EXTENDED WEAR ELECTROCARDIOGRAPHY PATCH, which claims priority to U.S. Provisional Patent App. No. 61/882,403, filed Sep. 25, 2013, titled LONG-TERM WEARABLE PHYSIOLOGICAL MONITOR. U.S. patent application Ser. No. 14/082,071 is also a continuation-in-part of U.S. patent application Ser. No. 14/080,725, filed Nov. 14, 2013, titled EXTENDED WEAR AMBULATORY ELECTROCARDIOGRAPHY AND PHYSIOLOGICAL SENSOR MONITOR, which claims priority to U.S. Provisional Patent App. No. 61/882,403, filed Sep. 25, 2013, titled LONG-TERM WEARABLE PHYSIOLOGICAL MONITOR. The entire contents of these applications are incorporated by reference herein in their entirely and relied upon.

FIELD

This application relates in general to electrocardiographic monitoring and, in particular, to an electrocardiography patch.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Diagnostic efficacy can be improved, when appropriate, through the use of long-term extended ECG monitoring. Recording sufficient ECG and related physiology over an extended period is challenging, and often essential to enabling a physician to identify events of potential concern. A 30-day observation period is considered the "gold standard" of ECG monitoring, yet achieving a 30-day observation day period has proven unworkable because such ECG monitoring systems are arduous to employ, cumbersome to the patient, and excessively costly. Ambulatory monitoring in-clinic is implausible and impracticable. Nevertheless, if a patient's ECG could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of ECG electrodes is complicated by skin irritation and the inability ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, Holter monitors are widely used for long-term extended ECG monitoring. Typically, they are used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter monitor (or event) can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic.

The ZIO XT Patch and ZIO Event Card devices, manufactured by iRhythm Tech., Inc., San Francisco, CA, are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components, including battery, and physical electrodes into a unitary assembly that adheres to the patient's skin. The ZIO XT Patch device uses adhesive sufficiently strong to support the weight of both the monitor and the electrodes over an extended period of time and to resist disadherance from the patient's body, albeit at the cost of disallowing removal or relocation during the monitoring period. Moreover, throughout monitoring, the battery is continually depleted and battery capacity can potentially limit overall monitoring duration. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of atrial (P-wave) signals.

In addition, with the advent of wireless communications and wearable computing, other types of personal ambulatory monitors, of varying degrees of sophistication, have become increasingly available. For example, adherents to the so-called "Quantified Self" movement combine wearable sensors and wearable computing to self-track activities of their daily lives, including inputs, states, and performance. The Nike+ FuelBand, manufactured by Nike Inc., Beaverton, OR, for instance, provides an activity tracker that is worn on the wrist and allows the wearer to temporally track the number of foot steps taken each day and an estimation of the calories burned. The activity tracker can interface with a smart phone device to allow a wearer to monitor their progress towards a fitness goal. Such quantified physiology, however, is typically tracked for only the personal use of the wearer and is not time-correlated to physician-supervised monitoring.

Therefore, a need remains for an extended wear continuously recording ECG monitor practicably capable of being worn for a long period of time in both men and women and capable of recording atrial signals reliably.

A further need remains for facilities to integrate wider-ranging physiological and "life tracking"-type data into long-term ECG and physiological data monitoring.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum, the area most likely to record high quality atrial signals or P-waves. The wearable monitor can also interoperate wirelessly with other wearable physiology and activity sensors and with wearable or mobile communications devices, including so-called "smart phones," to download monitoring data either in real-time or in batches. The monitor recorder can also be equipped with a wireless transceiver to either provide data or other information to, or receive data or other information from, an interfacing wearable physiology and activity sensor, or wearable or mobile communications devices for relay to a further device, such as a server, analysis, or other purpose.

One embodiment provides a remotely-interfaceable electrocardiography patch. The remotely-interfaceable electrocardiography patch includes a backing formed of a strip of material and an electrocardiographic electrode on each end of the backing to capture electrocardiographic signals. A flexible circuit includes a pair of circuit traces electrically coupled to the electrocardiographic electrodes. A wireless transceiver communicates at least one of the electrocardiographic signals and other physiological measures with one or more of a physiology and activity sensor, communication device, server, and personal computer.

A further embodiment provides an electrocardiography patch. The patch includes a backing and at least two electrocardiographic electrodes each positioned on the backing, across from another of the electrocardiographic electrodes, to capture electrocardiographic signals. A flexible circuit includes a pair of circuit traces electrically coupled to the electrocardiographic electrodes. A wireless transceiver communicates at least a portion of the electrocardiographic signals.

A still further embodiment provides an apparatus. A strip has first and second end sections, and a first surface and second surface. Two electrocardiographic electrodes are provided on the strip with one of the electrocardiographic electrodes provided on the first surface of the first end section of the strip and another of the electrocardiographic electrodes positioned on the first surface on the second end section of the strip. A flexible circuit is mounted to the second surface of the strip and includes a circuit trace electrically coupled to each of the electrocardiographic electrodes. A wireless transceiver is affixed on one of the first or second end sections, and a battery is positioned on one of the first or second end sections. A processor is positioned on one of the first or second end sections and is housed separate from the battery.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, would cause chafing, irritation, frustration, and annoyance, leading to low patient compliance.

The foregoing aspects enhance ECG monitoring performance and quality, facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis.

Finally, the foregoing aspects as relevant to monitoring are equally applicable to recording other physiological measures, such as temperature, respiratory rate, blood sugar, oxygen saturation, and blood pressure, as well as other measures of body chemistry and physiology.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
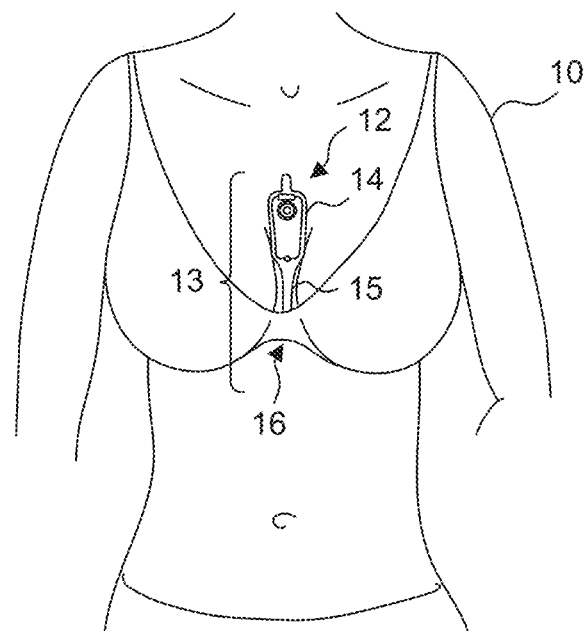
FIGS. 1 and 2 are diagrams showing, by way of examples, an extended wear electrocardiography and physiological sensor monitor respectively fitted to the sternal region of a female patient and a male patient.
Figure 2:
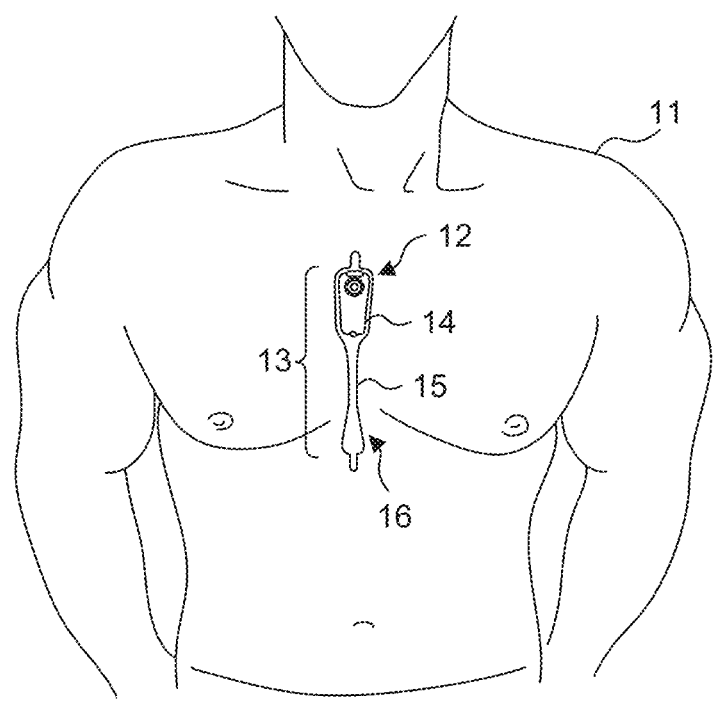

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity, while simultaneously facilitating comfortable long-term wear for many weeks. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the Xiphoid process facilitates sensing of ventricular activity and provides superior recordation of the QRS interval.

Figure 3:
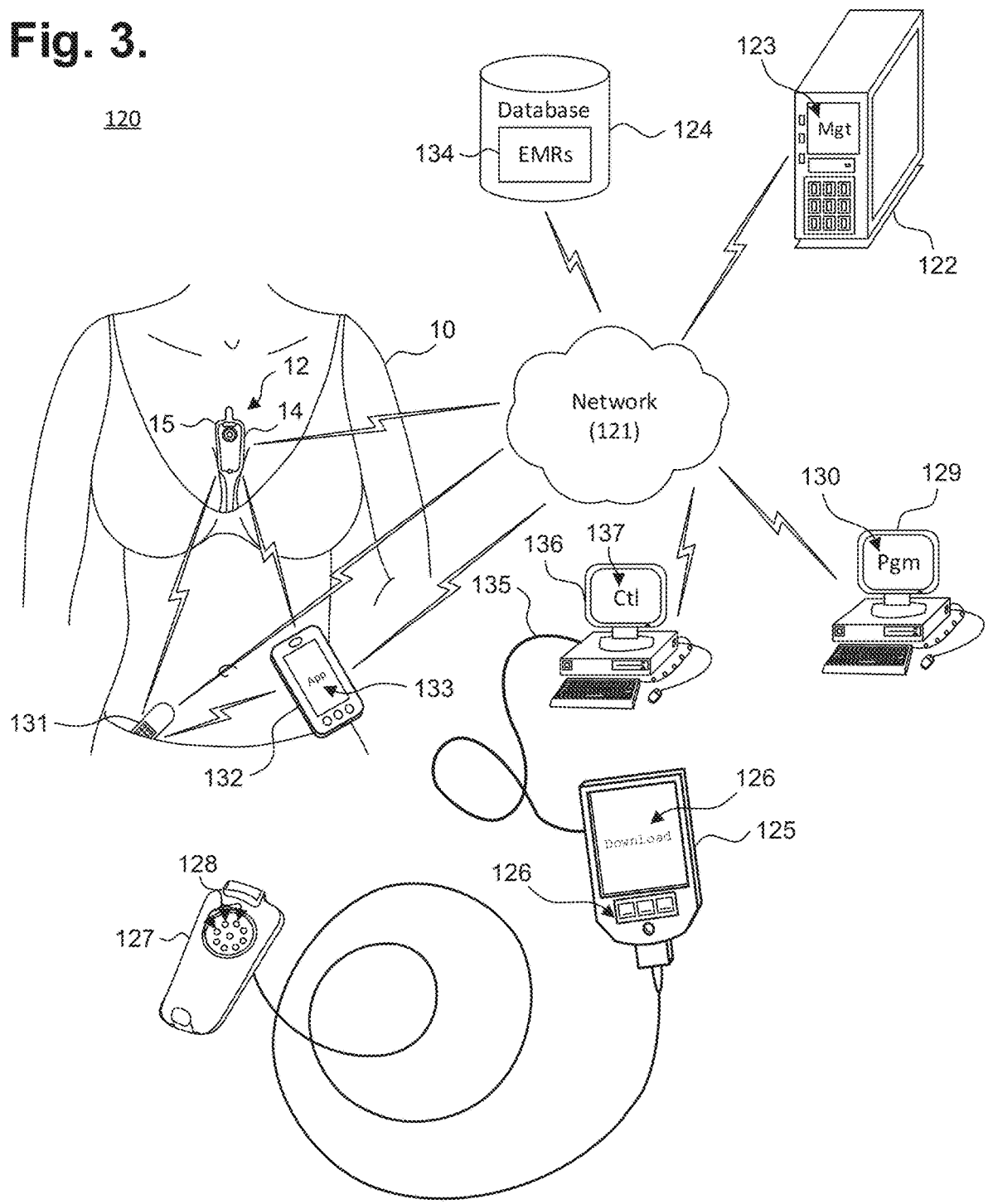
FIG. 3 is a functional block diagram showing a system for remote interfacing of an extended wear electrocardiography and physiological sensor monitor in accordance with one embodiment.

When operated standalone, the monitor recorder 14 of the extended wear electrocardiography and physiological sensor monitor 12 senses and records the patient's ECG data into an onboard memory. In addition, the wearable monitor 12 can interoperate with other devices. FIG. 3 is a functional block diagram showing a system 120 for remote interfacing of an extended wear electrocardiography and physiological sensor monitor 12 in accordance with one embodiment. The monitor recorder 14 is a reusable component that can be fitted during patient monitoring into a non-conductive receptacle provided on the electrode patch 15, as further described infra with reference to FIG. 4, and later removed for offloading of stored ECG data or to receive revised programming. The monitor recorder 14 can then be connected to a download station 125, which could be a programmer or other device that permits the retrieval of stored ECG monitoring data, execution of diagnostics on or programming of the monitor recorder 14, or performance of other functions. The monitor recorder 14 has a set of electrical contacts (not shown) that enable the monitor recorder 14 to physically interface to a set of terminals 128 on a paired receptacle 127 of the download station 125. In turn, the download station 125 executes a communications or offload program 126 ("Offload") or similar program that interacts with the monitor recorder 14 via the physical interface to retrieve the stored ECG monitoring data. The download station 125 could be a server, personal computer, tablet or handheld computer, smart mobile device, or purpose-built programmer designed specific to the task of interfacing with a monitor recorder 14. Still other forms of download station 125 are possible.

Figure 13:
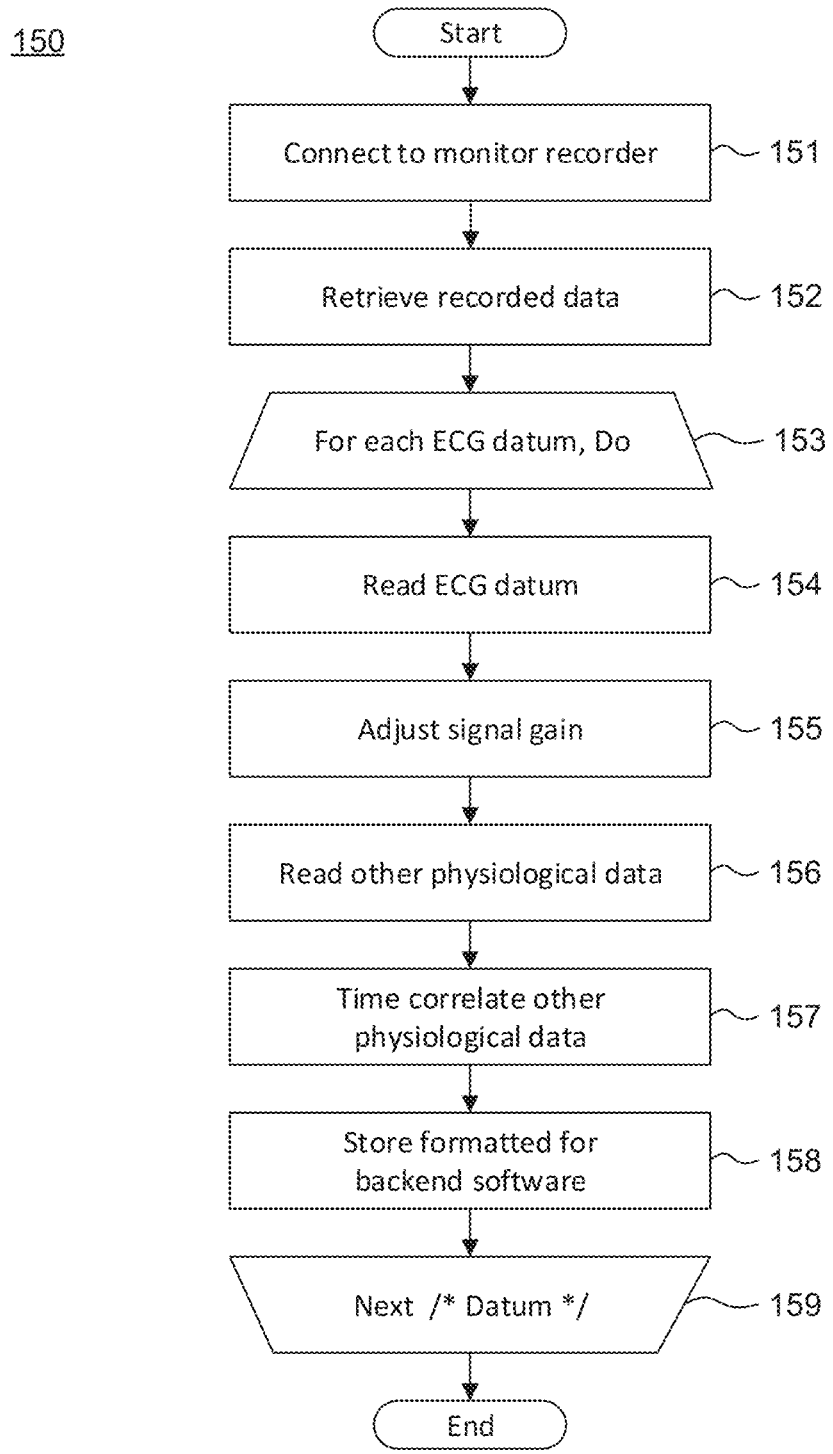
FIG. 13 is a flow diagram showing a method for offloading and converting ECG and other physiological data from an extended wear electrocardiography and physiological sensor monitor in accordance with one embodiment.

Upon retrieving stored ECG monitoring data from a monitor recorder 14, middleware first operates on the retrieved data to adjust the ECG capture quality, as necessary, and to convert the retrieved data into a format suitable for use by third party post-monitoring analysis software, as further described infra with reference to FIG. 13. The formatted data can then be retrieved from the download station 125 over a hard link 135 using a control program 137 ("Ctl") or analogous application executing on a personal computer 136 or other connectable computing device, via a communications link (not shown), whether wired or wireless, or by physical transfer of storage media (not shown). The personal computer 136 or other connectable device may also execute middleware that converts ECG data and other information into a format suitable for use by a third-party post-monitoring analysis program, as further described infra with reference to FIG. 13. Note that formatted data stored on the personal computer 136 would have to be maintained and safeguarded in the same manner as electronic medical records (EMRs) 134 in the secure database 124, as further discussed infra. In a further embodiment, the download station 125 is able to directly interface with other devices over a computer communications network 121, which could be some combination of a local area network and a wide area network, including the Internet, over a wired or wireless connection.

A client-server model could be used to employ a server 122 to remotely interface with the download station 125 over the network 121 and retrieve the formatted data or other information. The server 122 executes a patient management program 123 ("Mgt") or similar application that stores the retrieved formatted data and other information in a secure database 124 cataloged in that patient's EMRs 134. In addition, the patient management program 123 could manage a subscription service that authorizes a monitor recorder 14 to operate for a set period of time or under pre-defined operational parameters.

The patient management program 123, or other trusted application, also maintains and safeguards the secure database 124 to limit access to patient EMRs 134 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 124. The physician would execute an application program 130 ("Pgm"), such as a post-monitoring ECG analysis program, on a personal computer 129 or other connectable computing device, and, through the application 130, coordinate access to his patient's EMRs 134 with the patient management program 123. Other schemes and safeguards to protect and maintain the integrity of patient EMRs 134 are possible.

The wearable monitor 12 can interoperate wirelessly with other wearable physiology and activity sensors 131 and with wearable or mobile communications devices 133. Wearable physiology and activity sensors 131 encompass a wide range of wirelessly interconnectable devices that measure or monitor data physical to the patient's body, such as heart rate, temperature, blood pressure, and so forth; physical states, such as movement, sleep, footsteps, and the like; and performance, including calories burned or estimated blood glucose level. These devices originate both within the medical community to sense and record traditional medical physiology that could be useful to a physician in arriving at a patient diagnosis or clinical trajectory, as well as from outside the medical community, from, for instance, sports or lifestyle product companies who seek to educate and assist individuals with self-quantifying interests.

Frequently, wearable physiology and activity sensors 131 are capable of wireless interfacing with wearable or mobile communications devices 133, particularly smart mobile devices, including so-called "smart phones," to download monitoring data either in real-time or in batches. The wearable or mobile communications device 133 executes an application ("App") that can retrieve the data collected by the wearable physiology and activity sensor 131 and evaluate the data to generate information of interest to the wearer, such as an estimation of the effectiveness of the wearer's exercise efforts. Still other wearable or mobile communications device 133 functions on the collected data are possible.

The wearable or mobile communications devices 133 could also serve as a conduit for providing the data collected by the wearable physiology and activity sensor 131 to a server 122, or, similarly, the wearable physiology and activity sensor 131 could itself directly provide the collected data to the server 122. The server 122 could then merge the collected data into the wearer's EMRs 134 in the secure database 124, if appropriate (and permissible), or the server 122 could perform an analysis of the collected data, perhaps based by comparison to a population of like wearers of the wearable physiology and activity sensor 131. Still other server 122 functions on the collected data are possible.

Figure 9:
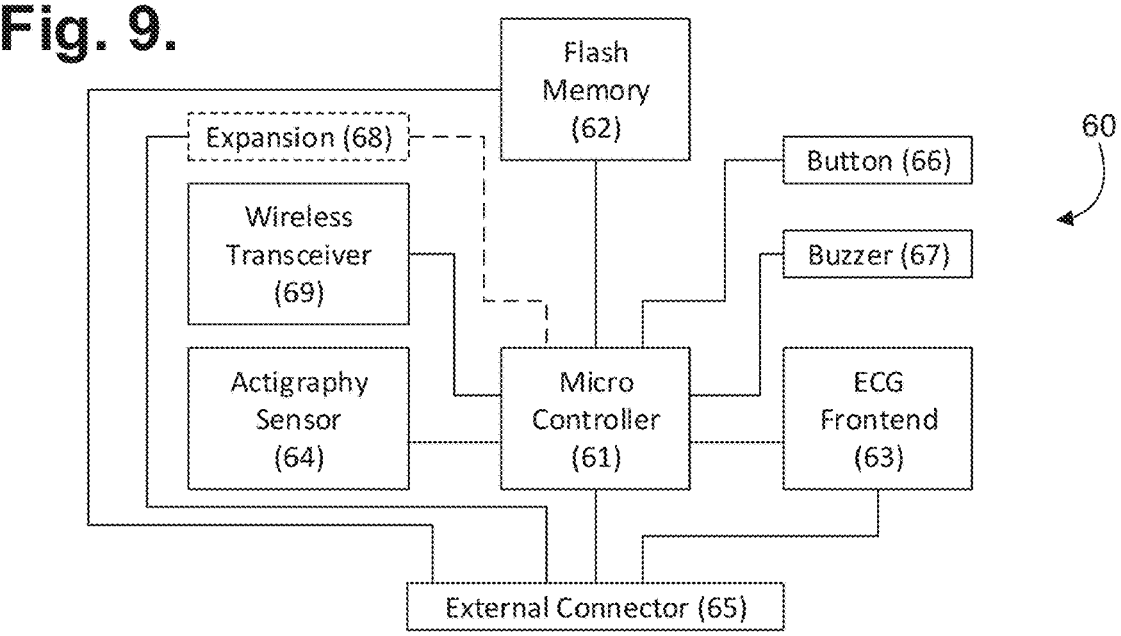
FIG. 9 is a functional block diagram showing the component architecture of the circuitry of the monitor recorder of FIG. 4.
Figure 10:
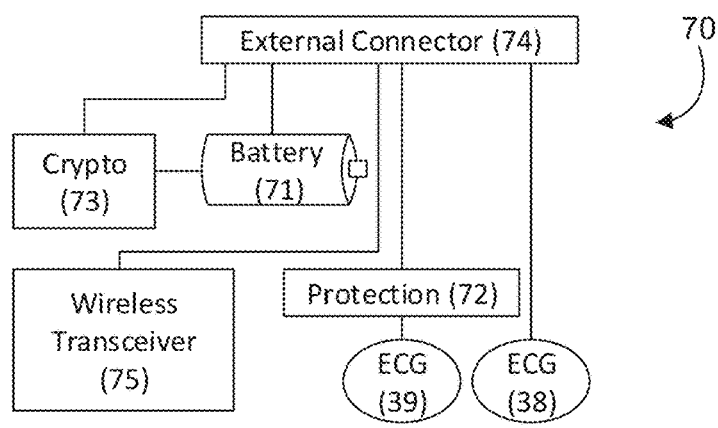
FIG. 10 is a functional block diagram showing the circuitry of the extended wear electrode patch of FIG. 4.

Finally, the monitor recorder 14 can also be equipped with a wireless transceiver, as further described infra with reference to FIGS. 9 and 10. Thus, when wireless-enabled, both wearable physiology and activity sensors 131 and wearable or mobile communications devices 133 could wirelessly interface with the monitor recorder 14, which could either provide data or other information to, or receive data or other information from an interfacing device for relay to a further device, such as the server 122, analysis, or other purpose. In addition, the monitor recorder 14 could wirelessly interface directly with the server 122, personal computer 129, or other computing device connectable over the network 121, when the monitor recorder 14 is appropriately equipped for interfacing with such devices. Still other types of remote interfacing of the monitor recorder 14 are possible.

Figure 4:
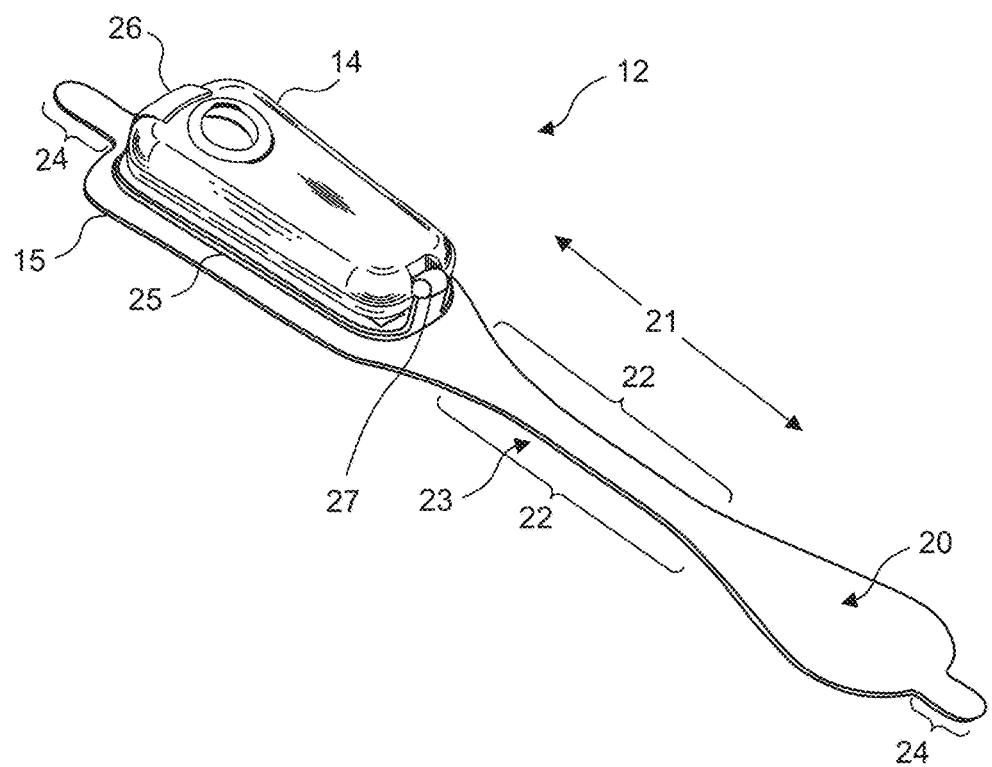
FIG. 4 is a perspective view showing an extended wear electrode patch with a monitor recorder inserted.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 4 is a perspective view showing an extended wear electrode patch 15 with a monitor recorder 14 in accordance with one embodiment inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Patent, entitled "Extended Wear Electrocardiography Patch," U.S. Pat. No. 9,545,204, issued Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Patent, entitled "Extended Wear Ambulatory Electrocardiography and Physiological Sensor Monitor," U.S. Pat. No. 9,730,593, issued Aug. 15, 2017, the disclosure which is incorporated by reference. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
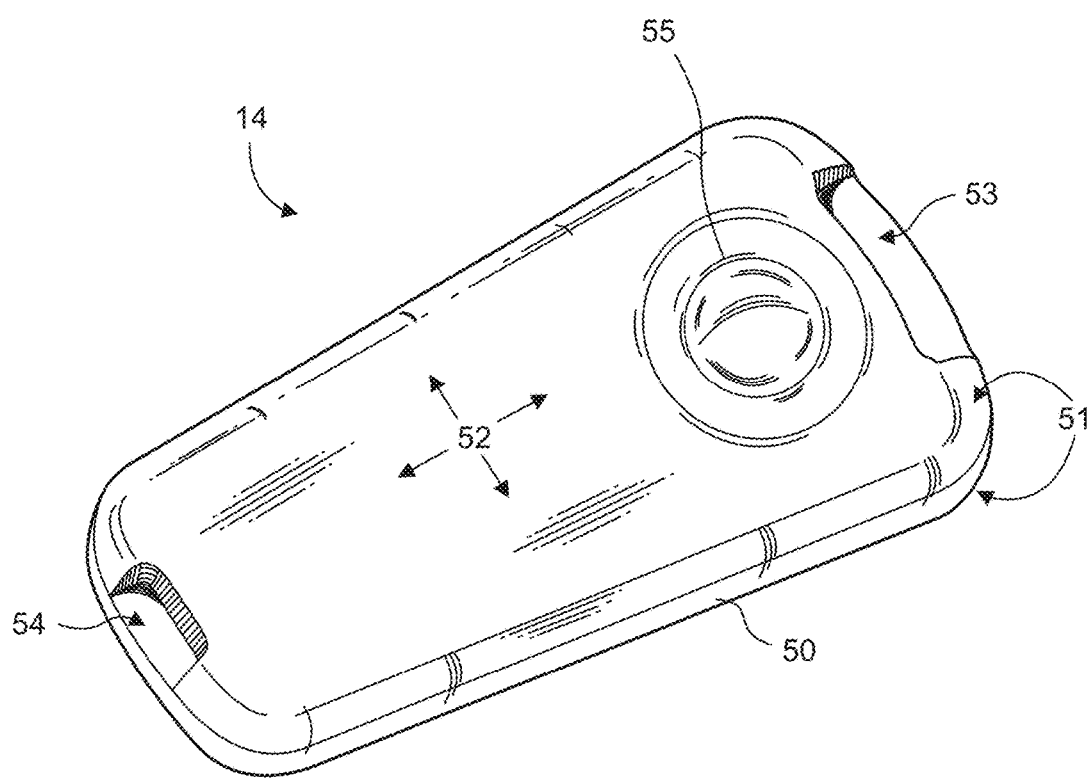
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Patent, entitled "Electrocardiography Monitor," No. D717,955, issued Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
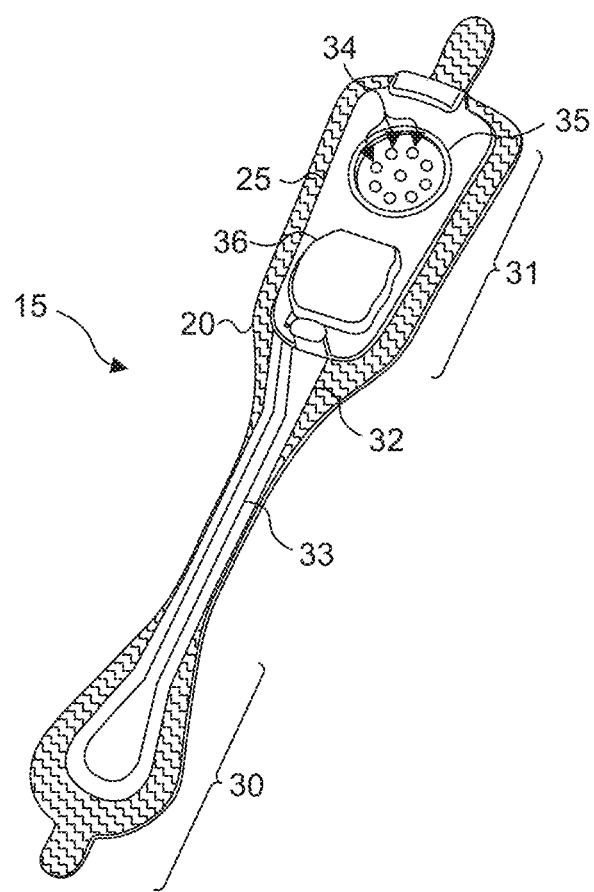
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 7:
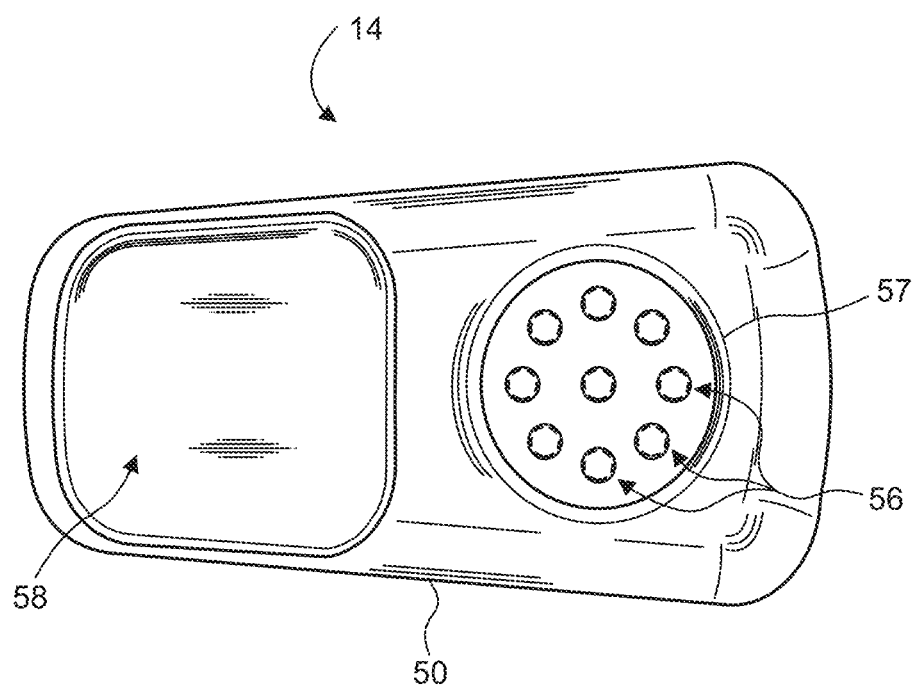
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 8:
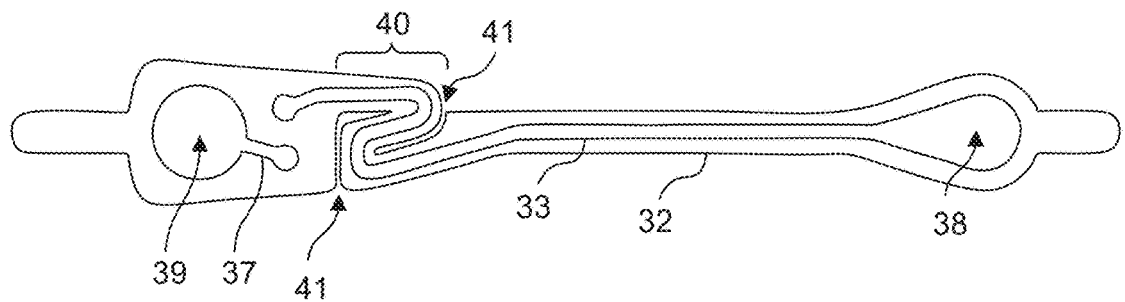
FIG. 8 is a top view showing the flexible circuit of the extended wear electrode patch of FIG. 4 when mounted above the flexible backing.

Unlike the flexible backing 20, the flexible circuit 32 is only able to bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

ECG monitoring and other functions performed by the monitor recorder 14 are provided through a micro controlled architecture. FIG. 9 is a functional block diagram showing the component architecture of the circuitry 60 of the monitor recorder 14 of FIG. 4. The circuitry 60 is externally powered through a battery provided in the non-conductive receptacle 25 (shown in FIG. 6). Both power and raw ECG signals, which originate in the pair of ECG electrodes 38, 39 (shown in FIG. 8) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions.

Operation of the circuitry 60 of the monitor recorder 14 is managed by a microcontroller 61. The micro-controller 61 includes a program memory unit containing internal flash memory that is readable and writeable. The internal flash memory can also be programmed externally. The microcontroller 61 draws power externally from the battery provided on the electrode patch 15 via a pair of the electrical contacts 56. The microcontroller 61 connects to the ECG front end circuit 63 that measures raw cutaneous electrical signals and generates an analog ECG signal representative of the electrical activity of the patient's heart over time.

The circuitry 60 of the monitor recorder 14 also includes a flash memory 62, which the micro-controller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses, such as described in commonly-assigned U.S. Pat. No. 9,737,224, issued Aug. 22, 2017, the disclosure of which is incorporated by reference.

The circuitry 60 of the monitor recorder 14 includes a wireless transceiver 69 that can provides wireless interfacing capabilities. The wireless transceiver 69 also draws power externally from the battery provided on the electrode patch 15 via a pair of the electrical contacts 56. The wireless transceiver 69 can be implemented using one or more forms of wireless communications, including the IEEE 802.11 computer communications standard, that is Wi-Fi; the 4G mobile phone mobile communications standard; the Bluetooth data exchange standard; or other wireless communications or data exchange standards and protocols. The type of wireless interfacing capability could limit the range of interoperability of the monitor recorder 14; for instance, Bluetooth-based implementations are designed for low power consumption with a short communications range.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the micro-controller 61 provided over one of the electrical contacts 56. The physiology sensor can include an $SpO_2$ sensor, blood pressure sensor, temperature sensor, respiratory rate sensor, glucose sensor, airflow sensor, volumetric pressure sensing, or other types of sensor or telemetric input sources. For instance, the integration of an airflow sensor is described in commonly-assigned U.S. Pat. No. 9,364,155, issued Jun. 14, 2016, the disclosure which is incorporated by reference.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

While the monitor recorder 14 operates under micro control, most of the electrical components of the electrode patch 15 operate passively. FIG. 10 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14, such as described in commonly-assigned U.S. Pat. No. 9,655,538, issued May 23, 2017, the disclosure which is incorporated by reference.

In a further embodiment, the circuitry 70 of the electrode patch 15 includes a wireless transceiver 75, in lieu the including of the wireless transceiver 69 in the circuitry 60 of the monitor recorder 14, which interfaces with the microcontroller 61 over the microcontroller's expansion port via the external connector 74.

Figure 11:
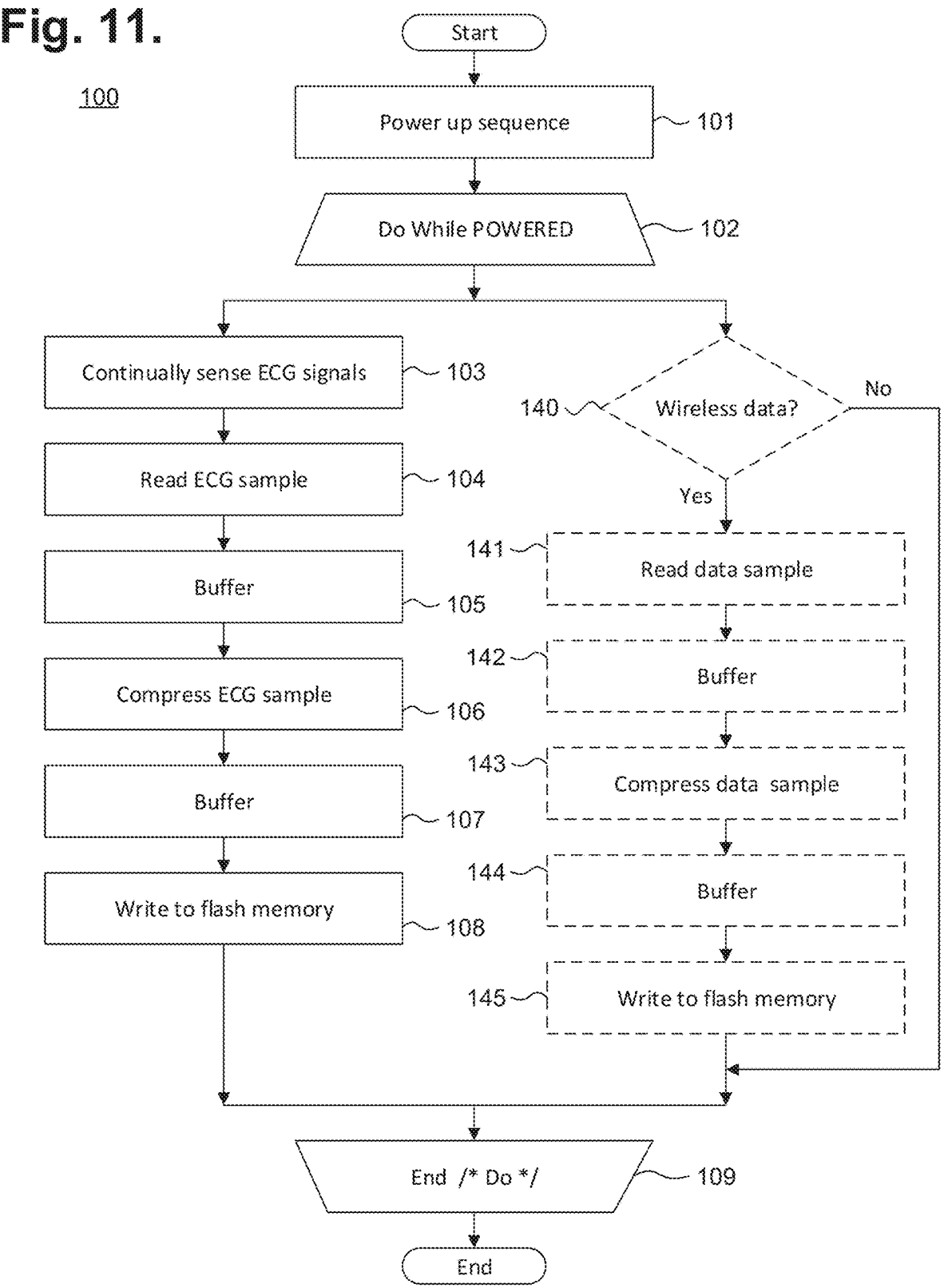
FIG. 11 is a flow diagram showing a monitor recorder-implemented method for monitoring ECG data for use in the monitor recorder of FIG. 4.

The monitor recorder 14 continuously monitors the patient's heart rate and physiology. FIG. 11 is a flow diagram showing a monitor recorder-implemented method 100 for monitoring ECG data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 12:
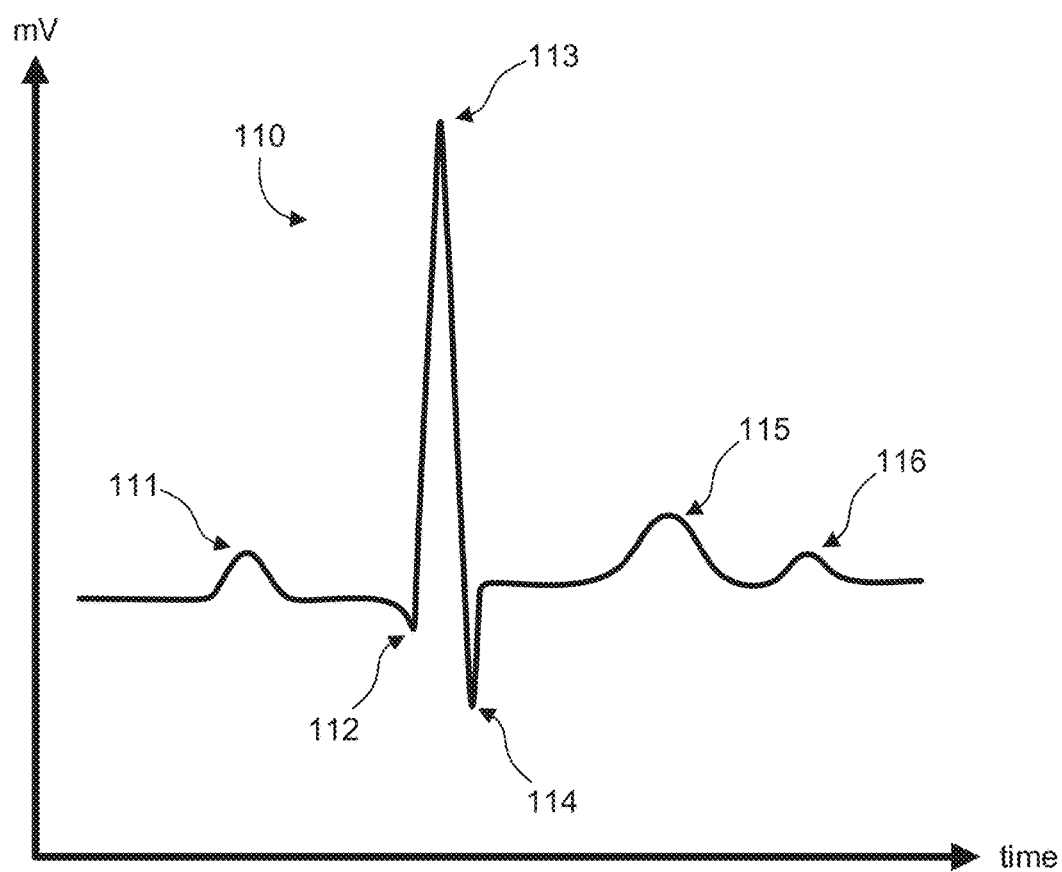
FIG. 12 is a graph showing, by way of example, a typical ECG waveform.

Following satisfactory completion of the power up sequence, an iterative processing loop (steps 102-109) is continually executed by the microcontroller 61. During each iteration (step 102) of the processing loop, the ECG frontend 63 (shown in FIG. 9) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal output front end 63. FIG. 12 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q wave 112, followed by a larger upward deflection of an R-wave 113, and terminated with a downward waveform of the S wave 114, collectively representative of ventricular depolarization. The T wave 115 is normally a modest upward waveform, representative of ventricular depolarization, while the U wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Each sampled ECG signal, in quantized and digitized form, is temporarily staged in buffer (step 105), pending compression preparatory to storage in the flash memory 62 (step 106). Following compression, the compressed ECG digitized sample is again buffered (step 107), then written to the flash memory 62 (step 108) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

In a further embodiment, the monitor recorder 14 also continuously receives data from wearable physiology and activity sensors 131 and wearable or mobile communications devices 133 (shown in FIG. 3). The data is received in a conceptually-separate execution thread as part of the iterative processing loop (steps 102-109) continually executed by the microcontroller 61. During each iteration (step 102) of the processing loop, if wireless data is available (step 140), a sample of the wireless is read (step 141) by the microcontroller 61 and, if necessary, converted into a digital signal by the onboard ADC of the microcontroller 61. Each wireless data sample, in quantized and digitized form, is temporarily staged in buffer (step 142), pending compression preparatory to storage in the flash memory 62 (step 143). Following compression, the compressed wireless data sample is again buffered (step 144), then written to the flash memory 62 (step 145) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

The monitor recorder 14 stores ECG data and other information in the flash memory 62 (shown in FIG. 9) using a proprietary format that includes data compression. As a result, data retrieved from a monitor recorder 14 must first be converted into a format suitable for use by third party post-monitoring analysis software. FIG. 13 is a flow diagram showing a method 150 for offloading and converting ECG and other physiological data from an extended wear electrocardiography and physiological sensor monitor 12 in accordance with one embodiment. The method 150 can be implemented in software and execution of the software can be performed on a download station 125, which could be a programmer or other device, or a computer system, including a server 122 or personal computer 129, such as further described supra with reference to FIG. 3, as a series of process or method modules or steps. For convenience, the method 150 will be described in the context of being performed by a personal computer 136 or other connectable computing device (shown in FIG. 3) as middleware that converts ECG data and other information into a format suitable for use by a third-party post-monitoring analysis program. Execution of the method 150 by a computer system would be analogous mutatis mutandis.

Initially, the download station 125 is connected to the monitor recorder 14 (step 151), such as by physically interfacing to a set of terminals 128 on a paired receptacle 127 or by wireless connection, if available. The data stored on the monitor recorder 14, including ECG and physiological monitoring data, other recorded data, and other information are retrieved (step 152) over a hard link 135 using a control program 137 ("Ctl") or analogous application executing on a personal computer 136 or other connectable computing device.

The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 153-159) in an iterative processing loop. During each iteration (step 153), the ECG datum is read (step 154) and, if necessary, the gain of the ECG signal is adjusted (step 155) to compensate, for instance, for relocation or replacement of the electrode patch 15 during the monitoring period.

In addition, depending upon the configuration of the wearable monitor 12, other physiological data (or other information), including patient events, such as a fall, peak activity level, sleep detection, Detection of patient activity levels and states, and so on, may be recorded along with the ECG monitoring data. For instance, actigraphy data may have been sampled by the actigraphy sensor 64 based on a sensed event occurrence, such as a sudden change in orientation due to the patient taking a fall. In response, the monitor recorder 14 will embed the actigraphy data samples into the stream of data, including ECG monitoring data, that is recorded to the flash memory 62 by the micro-controller 61. Post-monitoring, the actigraphy data is temporally matched to the ECG data to provide the proper physiological context to the sensed event occurrence. As a result, the three-axis actigraphy signal is turned into an actionable event occurrence that is provided, through conversion by the middleware, to third party post-monitoring analysis programs, along with the ECG recordings contemporaneous to the event occurrence. Other types of processing of the other physiological data (or other information) are possible.

Thus, during execution of the middleware, any other physiological data (or other information) that has been embedded into the recorded ECG monitoring data is read (step 156) and time-correlated to the time frame of the ECG signals that occurred at the time that the other physiological data (or other information) was noted (step 157). Finally, the ECG datum, signal gain adjusted, if appropriate, and other physiological data, if applicable and as time-correlated, are stored in a format suitable to the backend software (step 158) used in post-monitoring analysis.

In a further embodiment, the other physiological data, if apropos, is embedded within an unused ECG track. For example, the SCP-ENG standard allows multiple ECG channels to be recorded into a single ECG record. The monitor recorder 14, though, only senses one ECG channel. The other physiological data can be stored into an additional ECG channel, which would otherwise be zero-padded or altogether omitted. The backend software would then be able to read the other physiological data in context with the single channel of ECG monitoring data recorded by the monitor recorder 14, provided the backend software implemented changes necessary to interpret the other physiological data. Still other forms of embedding of the other physiological data with formatted ECG monitoring data, or of providing the other physiological data in a separate manner, are possible.

Processing continues (step 159) for each remaining ECG datum, after which the processing loop is exited and execution terminates. Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. A wearable electrocardiography monitoring device, comprising:
a flexible backing including a strip comprising:

a first face and a second face, wherein a portion of the first face is covered in adhesive to adhere the strip to skin of a patient, a first end section, a second end section opposite the first end section, and a mid-section between the first end section and the second end section;

a flexible circuit mounted to the second face of the strip, the flexible circuit comprising a first circuit trace and a second circuit trace;

a first electrocardiographic electrode and a second electrocardiographic electrode, wherein the first electrocardiographic electrode and the second electrocardiographic electrode are configured to sense electrocardiographic signals, wherein the first electrocardiographic electrode and the second electrocardiographic electrode are coupled to the flexible circuit, wherein the first electrocardiographic electrode is conductively exposed at the first face along the first end section of the strip, wherein the second electrocardiographic electrode is conductively exposed at the first face along the second end section of the strip, wherein the first circuit trace is electrically coupled to the first electrocardiographic electrode, and wherein the second circuit trace is electrically coupled to the second electrocardiographic electrode;

a battery;

a wireless transceiver;

a button configured to be pressed to mark an event;

a sealed housing having rounded edges on a top surface, wherein the sealed housing is coupled to the flexible backing, and wherein the sealed housing includes a processor, wherein the processor is electrically coupled to the first electrocardiographic electrode, the second electrocardiographic electrode, and the battery, wherein the processor is configured to process the electrocardiographic signals sensed via the first electrocardiographic electrode and the second electrocardiographic electrode.

2. The wearable electrocardiography monitoring device of claim 1, wherein the mid-section comprises a first edge parallel to a second edge.

3. The wearable electrocardiography monitoring device of claim 1, wherein the wireless transceiver is configured to communicate with an external device via Wi-Fi, mobile phone communication standards, or Bluetooth.

4. The wearable electrocardiography monitoring device of claim 1, wherein the electrocardiographic signals are converted to a different format.

5. The wearable electrocardiography monitoring device of claim 4, wherein the electrocardiographic signals are retrieved by one of a server, a client computer, and a mobile device via the wireless transceiver after the electrocardiographic signals are converted to the different format.

6. The wearable electrocardiography monitoring device of claim 1, wherein the adhesive covering the portion of the first face of the strip is provided on the first end section and the second end section only.

7. The wearable electrocardiography monitoring device of claim 1, wherein the battery is vertically aligned with the wireless transceiver.

8. A wearable electrocardiography monitoring device, comprising:
a flexible backing including a strip comprising:
a first face and a second face, wherein a portion of the first face is covered in adhesive to adhere the strip to skin of a patient, a first end section, a second end section opposite the first end section, and a mid-section between the first end section and the second end section, wherein the mid-section is narrower than the first end section and the second end section;

a flexible circuit mounted to the second face of the strip, the flexible circuit comprising a first circuit trace and a second circuit trace;

a first electrocardiographic electrode and a second electrocardiographic electrode, wherein the first electrocardiographic electrode and the second electrocardiographic electrode are configured to sense electrocardiographic signals, wherein the first electrocardiographic electrode and the second electrocardiographic electrode are coupled to the flexible circuit, wherein the first electrocardiographic electrode is conductively exposed at the first face along the first end section of the strip, wherein the second electrocardiographic electrode is conductively exposed at the first face along the second end section of the strip, wherein the first circuit trace is electrically coupled to the first electrocardiographic electrode, wherein the second circuit trace is electrically coupled to the second electrocardiographic electrode, and wherein the first electrocardiographic electrode includes an inline resistor;

a battery;

a wireless transceiver;

a button configured to be pressed to mark an event;

a sealed housing having rounded edges on a top surface, wherein the sealed housing is coupled to the flexible backing, and wherein the sealed housing includes a processor, wherein the processor is electrically coupled to the first electrocardiographic electrode, the second electrocardiographic electrode, and the battery, wherein the processor is configured to process the electrocardiographic signals sensed via the first electrocardiographic electrode and the second electrocardiographic electrode.

9. The wearable electrocardiography monitoring device of claim 8, wherein the battery is vertically aligned with the sealed housing.

10. The wearable electrocardiography monitoring device of claim 8, wherein the wireless transceiver is configured to communicate with an external device via Wi-Fi, mobile phone communication standards, or Bluetooth.

11. The wearable electrocardiography monitoring device of claim 8, wherein the electrocardiographic signals are converted to a different format.

12. The wearable electrocardiography monitoring device of claim 11, wherein the electrocardiographic signals are retrieved by one of a server, a client computer, and a mobile device via the wireless transceiver after the electrocardiographic signals are converted to the different format.

13. The wearable electrocardiography monitoring device of claim 8, wherein the adhesive covering the portion of the first face of the strip is provided on the first end section and the second end section only.

14. The wearable electrocardiography monitoring device of claim 8, wherein the battery is vertically aligned with the wireless transceiver.

15. A wearable electrocardiography monitoring device, comprising:
a flexible backing comprising:
a first face and a second face, wherein the first face includes an adhesive to adhere the flexible backing to skin of a patient;

a first end section opposite a second end section, wherein a mid-section is disposed between the first end section and the second end section, wherein the mid-section is narrower than the first end section and the second end section, and wherein the mid-section includes a first edge parallel to a second edge; and a flexible circuit, wherein the flexible circuit comprises a first circuit trace and a second circuit trace on the second face of the flexible backing;

a first electrocardiographic electrode configured to sense electrocardiographic signals, wherein the first electrocardiographic electrode is conductively exposed at the first face along the second end section of the flexible backing, and wherein the first electrocardiographic electrode is electrically coupled to the first circuit trace;

a second electrocardiographic electrode configured to sense electrocardiographic signals, wherein the second electrocardiographic electrode is conductively exposed at the first face along the first end section of the flexible backing, and wherein the second electrocardiographic electrode is electrically coupled to the second circuit trace;

a sealed housing having rounded edges on a top surface, wherein the sealed housing is coupled to the flexible backing, wherein the sealed housing includes a processor, wherein the processor is electrically coupled to the first electrocardiographic electrode and the second electrocardiographic electrode, wherein the processor is configured to process the electrocardiographic signals sensed via the first electrocardiographic electrode and the second electrocardiographic electrode;

a button disposed on the top surface of the sealed housing, wherein the button is configured to be pressed to mark an event;

a battery disposed between the processor and the skin of the patient, the battery configured to provide power to the processor of the sealed housing; and a wireless transceiver configured to communicate at least a portion of the electrocardiographic signals.

16. The wearable electrocardiography monitoring device of claim 15, wherein the wireless transceiver is configured to communicate with an external device via Wi-Fi, mobile phone communication standards, or Bluetooth.

17. The wearable electrocardiography monitoring device of claim 15, wherein the electrocardiographic signals are converted to a different format.

18. The wearable electrocardiography monitoring device of claim 17, wherein the electrocardiographic signals are retrieved by one of a server, a client computer, and a mobile device via the wireless transceiver after the electrocardiographic signals are converted to the different format.

19. The wearable electrocardiography monitoring device of claim 15, wherein the adhesive covering the portion of the first face is provided on the first end section and the second end section only.

20. The wearable electrocardiography monitoring device of claim 15, wherein the battery is vertically aligned with the wireless transceiver.

21. The wearable electrocardiography monitoring device of claim 15,
wherein the wireless transceiver is configured to communicate with an external device via Wi-Fi, mobile phone communication standards, or Bluetooth,
wherein the electrocardiographic signals are converted to a different format,
wherein the electrocardiographic signals are retrieved by one of a server, a client computer, and a mobile device via the wireless transceiver after the electrocardiographic signals are converted to the different format,
wherein the adhesive covering the portion of the first face is provided on the first end section and the second end section only, and
wherein the battery is vertically aligned with the wireless transceiver.

22. The wearable electrocardiography monitoring device of claim 15,
wherein the wireless transceiver is configured to communicate with an external device via Wi-Fi, mobile phone communication standards, or Bluetooth,
wherein the electrocardiographic signals are retrieved by one of a server, a client computer, and a mobile device via the wireless transceiver after the electrocardiographic signals are converted to a different format,
wherein the adhesive covering the portion of the first face is provided on the first end section and the second end section only, and
wherein the battery is vertically aligned with the wireless transceiver.

23. The wearable electrocardiography monitoring device of claim 15,
wherein the wireless transceiver is configured to communicate with an external device via Wi-Fi, mobile phone communication standards, or Bluetooth,
wherein the electrocardiographic signals are converted to a different format,
wherein the adhesive covering the portion of the first face is provided on the first end section and the second end section only, and
wherein the battery is vertically aligned with the wireless transceiver.

24. The wearable electrocardiography monitoring device of claim 15,
wherein the wireless transceiver is configured to communicate with an external device via Wi-Fi, mobile phone communication standards, or Bluetooth,
wherein the electrocardiographic signals are converted to a different format,
wherein the electrocardiographic signals are retrieved by one of a server, a client computer, and a mobile device via the wireless transceiver after the electrocardiographic signals are converted to the different format, and
wherein the battery is vertically aligned with the wireless transceiver.

25. The wearable electrocardiography monitoring device of claim 15,
wherein the wireless transceiver is configured to communicate with an external device via Wi-Fi, mobile phone communication standards, or Bluetooth,
wherein the electrocardiographic signals are converted to a different format,
wherein the electrocardiographic signals are retrieved by one of a server, a client computer, and a mobile device via the wireless transceiver after the electrocardiographic signals are converted to the different format, and
wherein the adhesive covering the portion of the first face is provided on the first end section and the second end section only.

26. The wearable electrocardiography monitoring device of claim 15,
wherein the wireless transceiver is configured to communicate with an external device via Wi-Fi, mobile phone communication standards, or Bluetooth, wherein the electrocardiographic signals are converted to a different format, and wherein the electrocardiographic signals are retrieved by one of a server, a client computer, and a mobile device via the wireless transceiver after the electrocardiographic signals are converted to the different format.

27. The wearable electrocardiography monitoring device of claim 15, wherein the wireless transceiver is configured to communicate with an external device via Wi-Fi, mobile phone communication standards, or Bluetooth, wherein the electrocardiographic signals are converted to a different format, and wherein the adhesive covering the portion of the first face is provided on the first end section and the second end section only.

28. The wearable electrocardiography monitoring device of claim 15, wherein the wireless transceiver is configured to communicate with an external device via Wi-Fi, mobile phone communication standards, or Bluetooth, wherein the electrocardiographic signals are converted to a different format, and wherein the battery is vertically aligned with the wireless transceiver.

29. The wearable electrocardiography monitoring device of claim 15, wherein the wireless transceiver is configured to communicate with an external device via Wi-Fi, mobile phone communication standards, or Bluetooth, wherein the electrocardiographic signals are retrieved by one of a server, a client computer, and a mobile device via the wireless transceiver after the electrocardiographic signals are converted to a different format, and wherein the adhesive covering the portion of the first face is provided on the first end section and the second end section only.

30. The wearable electrocardiography monitoring device of claim 15, wherein the wireless transceiver is configured to communicate with an external device via Wi-Fi, mobile phone communication standards, or Bluetooth, wherein the electrocardiographic signals are retrieved by one of a server, a client computer, and a mobile device via the wireless transceiver after the electrocardiographic signals are converted to a different format, and wherein the battery is vertically aligned with the wireless transceiver.

* * * * *

UNITED STATES PATENT AND TRADEMARK OFFICE
CERTIFICATE OF CORRECTION

| | | |
|---|---|---|
| PATENT NO. | : 12,171,562 B1 | Page 1 of 1 |
| APPLICATION NO. | : 18/821409 | |
| DATED | : December 24, 2024 | |
| INVENTOR(S) | : Jason Felix, Jon Mikalson Bishay and Gust H. Bardy | |

It is certified that error appears in the above-identified patent and that said Letters Patent is hereby corrected as shown below:

On the Title Page

Item (54) and in the Specification, Column 1, Line 1. The Title of the Invention should read: "ELECTROCARDIOGRAPHY PATCH" instead of "ELECTROCARDIOGRAMY PATCH".

Signed and Sealed this
Eleventh Day of February, 2025

Coke Morgan Stewart
*Acting Director of the United States Patent and Trademark Office*